United States Patent [19]

Klingler et al.

[11] Patent Number: 5,399,570
[45] Date of Patent: Mar. 21, 1995

[54] ASPARTIC ACID DERIVATIVES, AND THEIR USE FOR INHIBITING PLATELETE AGGREGATION

[75] Inventors: Otmar Klingler, Rodgau; Gerhard Zoller, Schöneck; Melitta Just, Langen; Bernd Jablunka, Bad Soden, all of Germany

[73] Assignee: Cassella Aktiengesellschaft, Frankfurt am Main, Germany

[21] Appl. No.: 36,923

[22] Filed: Mar. 25, 1993

[30] Foreign Application Priority Data

Apr. 13, 1992 [DE] Germany .................. 42 12 304.6

[51] Int. Cl.$^6$ ................ A61K 31/445; C07D 211/08; C07D 211/44
[52] U.S. Cl. ..................... 514/327; 514/331; 514/428; 514/674; 546/216; 546/231; 548/566; 564/230; 564/237
[58] Field of Search ............... 546/216, 231; 514/327, 514/331, 428, 634; 564/230, 237; 548/566

[56] References Cited

U.S. PATENT DOCUMENTS

| | | | |
|---|---|---|---|
| 4,879,313 | 11/1989 | Tjoeng et al. | 514/616 |
| 5,084,466 | 1/1992 | Alig et al. | 514/353 |
| 5,086,069 | 2/1992 | Klein et al. | 514/399 |
| 5,227,490 | 7/1993 | Hartman et al. | 514/317 |
| 5,264,420 | 11/1993 | Duggan et al. | 514/19 |

FOREIGN PATENT DOCUMENTS 502536 9/1992 European Pat. Off. .

WO90/15620 12/1990 WIPO .
WO91/04746 4/1991 WIPO .

OTHER PUBLICATIONS

Ruoslahti et al "New Perspective in Cell Adhesion" Science 238 491–492 (1987).
J. Med. Chem. (1992), vol. 35, pp. 4914–4917, Zablocki et al.
J. Med. Chem. (1991) vol. 34, pp. 3114–3125, Samanen et al.

*Primary Examiner*—Celia Chang
*Attorney, Agent, or Firm*—Perman & Green

[57] ABSTRACT

Aspartic acid derivatives of the formula

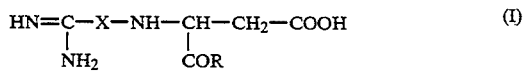

in which X denotes, for example,

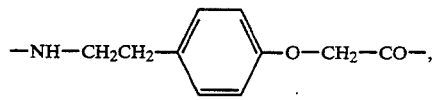

and R denotes, for example, cyclohexylamino, have useful pharmacological properties.

10 Claims, No Drawings

ASPARTIC ACID DERIVATIVES, AND THEIR USE FOR INHIBITING PLATELETE AGGREGATION

The invention relates to aspartic acid derivatives of the general formula I $$HN=C-X-NH-CH-CH_2-COOH \quad (I)$$
$$\phantom{HN=C-}|\phantom{X-NH-}|$$
$$\phantom{HN=C-}NH_2 \phantom{X-NH-}COR$$

in which
X denotes

−NH−(CH$_2$)$_n$−⌬−CO−N(CH$_3$)−CH$_2$−CO−,

−N(−CH$_2$−CH$_2$−(CH$_2$)$_k$)−A−⌬−CO−,

−NH−(CH$_2$)$_m$−⌬−CO−N(CH$_3$)−CH$_2$−CO−,

−NH−(CH$_2$)$_m$−⌬−O−CH$_2$−CO−,

A denotes —(CH$_2$)$_m$—, —O— or a direct bond,
n denotes a number from 1 to 4,
k denotes a number from 0 to 7,
m denotes a number from 0 to 4,
R denotes

−OR$^1$, −N(R$^2$)−R$^3$, −NH−R$^4$, $R^1$ denotes hydrogen, $C_1$-$C_{28}$alkyl, $C_3$-$C_{28}$cycloalkyl, phenyl, where the $C_1$-$C_{28}$alkyl, the $C_3$-$C_{28}$cycloalkyl or the phenyl is unsubstituted or mono- or polysubstituted by identical or different radicals from the series consisting of hydroxyl, carboxyl, $C_1$-$C_4$alkoxycarbonyl, arylmethoxycarbonyl, carboxamido, $C_1$-$C_4$alkylaminocarbonyl, amino, mercapto, $C_1$-$C_4$alkoxy, $C_3$-$C_8$cycloalkyl, imidazolyl, indolyl, pyrrolidinyl, hydroxypyrrolidinyl, halogen, phenyl or phenoxy, each of which is unsubstituted or monosubstituted or polysubstituted by hydroxyl, $C_1$-$C_4$alkyl, halogen, nitro or trifluoromethyl, $C_3$-$C_{81}$alkyl interrupted one or more times by —O— and ($C_3$-$C_{81}$alkoxy)carbonyl interrupted one ore more times by —O—;

$R^2$ and $R^3$ independently of one another denoted hydrogen, $R^1$ or, together with the nitrogen to which they are bonded, a 5- or 6-membered, saturated heterocyclic ring which can additionally contain —O— or —NR$^5$,
or $R^2$ denotes hydrogen and $R^3$ denotes a radical of the formula $$\begin{array}{l} R^6 \phantom{-CO-O-}CH_2-O-CO-(CH_2)_p-CH_3 \\ |\phantom{-CO-O-CH}| \\ -CH-CO-O-CH \\ \phantom{-CH-CO-O-}| \\ \phantom{-CH-CO-O-}CH_2-O-CO-(CH_2)_q-CH_3 \end{array}$$

or $$\begin{array}{l} R^6 \\ | \\ -CH-CO-O-CH_3 \\ |\\ CH-O-CO-(CH_2)_p-CH_3 \\ | \\ CH_2-O-CO-(CH_2)_q-CH_3 \end{array}$$

$R^4$ denotes the radical of an amino acid or of a dipeptide, in which the peptide bond can also be reduced to —NH—CH$_2$—, $R^5$ denotes hydrogen, $C_1$-$C_4$alkyl, phenyl, $C_1$-$C_4$alkylphenyl, $C_1$-$C_4$alkoxyphenyl, $R^6$ denotes hydrogen, $C_1$-$C_4$alkyl, phenyl, phenyl($C_1$-$C_4$)alkyl, p and q independently of one another denote a number from 1 to 20, and their physiologically tolerable salts.

The invention also relates to the processes for the preparation of the compounds of the formula I and their use as pharmaceutically active substances.

The alkyl and alkoxy radicals representing $R^1$, $R^2$, $R^3$ and $R^5$ can be straight-chain or branched. This also applies if they carry substituents or occur as substituents of other radicals.

Examples of suitable $C_1$-$C_{28}$alkyl radicals are: methyl, ethyl, propyl, butyl, pentyl, hexyl, heptyl, octyl, decyl, dodecyl, tridecyl, heptadecyl, nonadecyl, eicosyl, docosyl, tricosyl, pentacosyl, hexacosyl, heptacosyl, octacosyl, isobutyl, isopentyl, neopentyl, isohexyl, 3-methylpentyl, 2,3,5-trimethylhexyl, sec-butyl, tert-butyl, tert-pentyl, isohexyl. Unbranched $C_1$-$C_{28}$alkyl radicals are preferred.

Of the $C_3$-$C_{28}$cycloalkyl radicals, $C_3$-$C_8$alkyl radicals (cyclopropyl, cyclobutyl, cyclopentyl, cyclohexyl, cycloheptyl, cyclooctyl), in particular cyclopentyl and cyclohexyl, are preferred.

Halogen can be, for example, fluorine, chlorine, bromine or iodine, of which fluorine, chlorine and bromine are preferred.

The $C_3$-$C_{81}$alkyl interrupted one or more times by oxygen preferably contains the group $$H_3CO\text{\textendash}(CH_2CH_2O)_{\overline{x}}$$

where x is a number from 1 to 40.

The ($C_3$-$C_{81}$alkoxy)carbonyl interrupted one or more times by oxygen preferably contains the group $$H_3CO\text{\textendash}(CH_2CH_2O)_{\overline{x}}CO-$$

where x is a number from 1 to 40.

The $C_3$-$C_8$cycloalkyl radicals can in particular also be substituted by a carboxyl group.

The aryl radical in the arylmethoxycarbonyl radical can be, for example, an α- or β-naphthyl radical or in particular a phenyl radical.

A phenyl or phenoxy radical acting for $R^1$, $R^2$, $R^3$ or a phenyl or phenoxy radical acting as a substituent for $R^1$, $R^2$ or $R^3$ can be, for example, mono-, di- or trisubstituted, if this is possible for steric reasons or for stability reasons. In the case of nitro substitution, as a rule only one nitro group, if appropriate in addition to other substituents, is present.

The imidazole radical is in particular a 4-imidazole radical. The indolyl radical is in particular a 3-indolyl radical.

Suitable substituted phenyl radicals are, for example, 3,5-dibromo-4-hydroxyphenyl.

$R^2$ and $R^3$, together with the nitrogen to which they are bonded, can also form a 5- or 6-membered saturated heterocyclic ring which can additionally contain —O— or —N($R^5$)—. Examples of radicals of this type are 1-pyrrolidinyl, piperidino, morpholino, 1-piperazinyl, 4-($C_1$–$C_4$alkyl)piperazin-1-yl, in particular 4-methylpiperazin-1-yl, 4-phenylpiperazin-1-yl, 4-($C_1$–$C_4$alkoxy)-piperazin-1-yl.

Hydrogen is preferred for $R^2$.

$R^4$ represents the radical of a natural or unnatural amino acid or of a dipeptide, this radical formally being formed by removal of an $NH_2$ group from the amino acid or the dipeptide. Radicals of β-amino acids and in particular of α-amino acids are preferred. The radicals $R^4$ can be derived, for example, from the following amino acids, which, if they are chiral, can be present in the D- or L-form (cf. Houben-Weyl, Methoden der organischen Chemie (Methods of Organic Chemistry, volume XV/1 and 2, Stuttgart, 1974): Aad, Abu, δAbu, Bz, 2ABz, εAca, Ach, Acp, Adpd, Ahb, Aib, βAib, Ala, βAla, ΔAla, Alg, All, Ama, Amt, Ape, Apm, Apr, Arg, Ash, Asp, Asu, Aze, Azi, Bai, Bph, Can, Cit, Cys, (Cys)$_2$, Cyta, Daad, Dab, Dadd, Dap, Dapm, Dasu, Djen, Dpa, Dtc, Fel, Gln, Glu, Gly, Guy, hAla, hArg, hCys, hGln, hGlu, His, hIle, bleu, hLys, hMet, hPhe, hPro, hSer, hThr, hTrp, hTyr, Hyl, Hyp, 3Hyp, Ile, Ise, Ira, Kyn, Lant, Lcn, Leu, Lsg, Lys, βLys, ΔLys, Met, Mim, Min, nArg, Nle, Nva, Oly, Orn, Pan, Pec, Pen, Phe, Phg, Pic, Pro, ΔPro, Pse, Pya, Pyr, Pza, Qin, Ros, Sat, Sec, Sem, Ser, Thi, βThi, Thr, Thy, Thx, Tia, Tle, Tly, Trp, Trta, Tyr, Val, Tbg, Npg, Chg, Cha, Thia, 2,2-diphenylaminoacetic acid, 2-(p-tolyl)-2-phenylaminoacetic acid, 2-(p-chlorophenyl)aminoacetic acid.

The radical $R^4$ can also be derived from a dipeptide, it being possible for these dipeptides to contain, as components, natural or unnatural amino acids. In addition, the radicals $R^4$ of the natural or unnatural amino acids and dipeptides can also be present as esters or amides, such as, for example, the methyl ester, ethyl amide, semicarbazide or ω-amino-($C_4$–$C_8$)alkyl amide.

Functional groups of the amino acid and dipeptide radicals $R^4$ can be present in protected form. Suitable protective groups such as, for example, urethane protective groups, carboxyl protective groups and side-chain protective groups are described in Hubbuch, Kontakte (Merck) 1979, No. 3, pages 14 to 23 and in Büllesbach, Kontakte (Merck) 1980, No. 1, pages 23 to 35. The following may in particular be mentioned: Aloc, Pyoc, Fmoc, Tcboc, Z, Boc, Ddz, Bpoc, Adoc, Msc, Moc, Z($NO_2$), Z(Hal$_n$), Bobz, Iboc, Adpoc, Mboc, Acm, tert-butyl, OBzl, ONbzl, OMbzl, Bzl, Mob, Pic, Trt.

—N($R^2$)$R^3$ and in particular —NH—$R^4$ is preferred for R. The radical —N($R^2$)$R^3$ in particular denotes an amino-($C_1$–$C_8$)alkyldiphenyl radical, an amino-($C_3$–$C_8$)cycloalkyl radical or an amino-($C_1$–$C_8$)-alkyl radical. The amino-($C_3$–$C_8$)cycloalkyl radical can in this case also be substituted on the cycloalkyl radical, in particular by a carboxyl group. The amino-($C_1$–$C_8$)alkyldiphenyl radical is in particular an ω, ω-diphenylalkylamine radical, very particularly preferably a 3,3-diphenylpropylamine radical. Particularly preferably, the radical —NH—$R^4$ representing R represents the valine, phenylalanine or phenylglycine radical, which is formed by removal of a hydrogen atom from the amino group of valine, phenylalanine or phenylglycine.

Hydrogen, phenyl, benzyl, methyl or isopropyl are preferred for $R^6$.

2 and in particular 3 are preferred for k. A number from 14 to 16 is preferred for p and q.

The radicals representing X preferably contain 1,4- or 1,3-phenylene, 1,4-cyclohexylene, p-piperidinyl or 3-pyrrolidinyl.

1 is preferred for n and 1 or 2 are preferred for m.

Particularly preferred radicals X are:

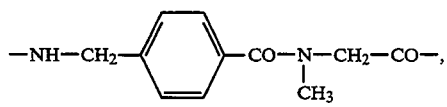

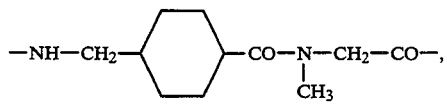

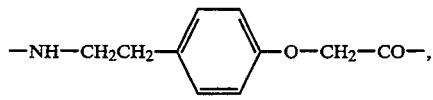

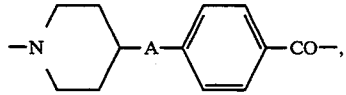

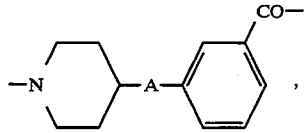

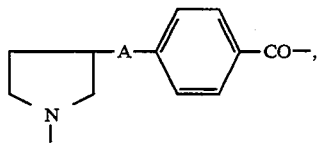

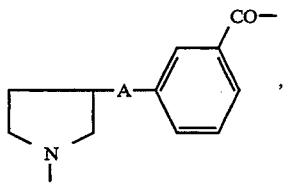

Preferred compounds of the formula I are those which contain one and in particular several of the preferred radicals or groups.

Physiologically tolerable salts of the compounds of the general formula I are in particular pharmaceutically utilisable or non-toxic salts.

The carboxyl group of the compounds of the formula I can form salts with alkali metals or alkaline earth metals, such as, for example, Na, K, Mg and Ca, and also with physiologically tolerable organic amines, such as, for example, triethylamine and tris(2-hydroxyethyl-)amine.

Compounds of the general formula I can also form salts on the basic amidino group or guanidino group with inorganic acids and with organic carboxylic or sulphonic acids.

Compounds of the formula I can be prepared by a) reacting a compound of the general formula II $$HN=C-Z-COOH \quad \text{(II)}$$
$$\phantom{HN=C-}|$$
$$\phantom{HN=C-}NH_2$$

in which
Z denotes

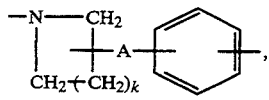

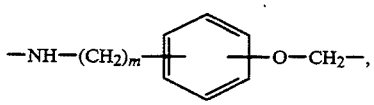

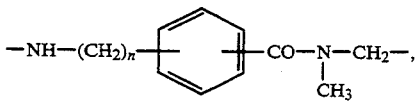

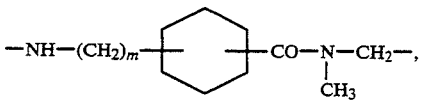

and A, n and m have the meanings already mentioned, with a compound of the general formula III $$H_2N-CH-CH_2-COOH \quad \text{(III)}$$
$$\phantom{H_2N-}|$$
$$\phantom{H_2N-}COR$$

in which R has the meaning already mentioned, or b) reacting a compound of the general formula IIa $$HN=C-Z^1-COOH \quad \text{(IIa)}$$
$$\phantom{HN=C-}|$$
$$\phantom{HN=C-}NH_2$$

in which
$Z^1$ denotes

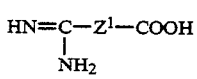

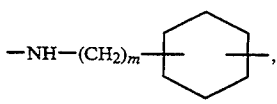

and n and m have the meaning already mentioned, with a compound of the general formula IIIa $$H-N-CH_2-CO-NH-CH-CH_2-COOH \quad \text{(IIIa)}$$
$$\phantom{H-N-}| \phantom{CH_2-CO-NH-}|$$
$$\phantom{H-N-}CH_3 \phantom{CH_2-CO-NH-}COR$$

in which
R has the meaning already mentioned, or c) reacting a compound of the general formula Ia $$HN=C-X-NH-CH-CH_2-COY^1 \quad \text{(Ia)}$$
$$\phantom{HN=C-}| \phantom{X-NH-}|$$
$$\phantom{HN=C-}NH_2 \phantom{X-NH-}COOH$$

in which X has the meaning already mentioned at the beginning and $Y^1$ denotes a protective group, with a compound of the formula IV $$HR \quad \text{(IV)}$$

in which R has the meaning already mentioned at the beginning, and then removing the protective group, and by optionally converting the compound of the formula I into a physiologically tolerable salt.

The reactions for the preparation of the compounds of the formula I according to the invention are in principle acylation reactions. They are carried out according to known principles, in particular according to the known methods of peptide chemistry (cf., for example, Houben-Weyl, Methoden der organischen Chemie, (Methods of Organic Chemistry, vol. 15/2 (1974); Ullmanns Enzyklopädie der techn. Chemie, (Ullman's Encylopedia of Industrial Chemistry, 4th edition, vol. 19, pp. 542–548). Groups present which are not intended to react are protected by protective groups which are removed again after the reaction. All protective groups can be used which are stable under the synthesis conditions and can be removed again after the synthesis of the compounds according to the invention. Suitable amino protective groups are, for example (the customary abbreviations are in brackets): benzyloxycarbonyl (Z), tert-butoxycarbonyl (Boc), 3,5-dimethoxyphenyliso-propoxycarbonyl (Ddz), 2-(4-biphenyl)-iso-propoxycarbonyl (Bpoc), trityl (Trt), methyl-sulphonylethoxycarbonyl (Msc), 9-fluorenylmethylcarbonyl (Fmoc). Guanidino groups can be protected, for example, with $NO_2$ groups or with methoxytrimethylbenzenesulphonyl (Mtr) groups. Methyl or ethyl esters, tert-butyl esters, allyl, benzyl or nitrobenzyl esters are used as carboxyl protective groups.

Suitable sulphur protective groups for mercapto radicals present in the molecule are, for example, benzyl (Bzl), p-methoxybenzyl (Mzl), trityl (Trt) or acetamidomethyl (Acm).

The conditions for the introduction and removal of the protective groups are known from peptide chemistry (cf., for example, Houben-Weyl loc. cit., Ullmanns loc. cit.).

$NO_2$ groups (guanidino protection), benzyloxycarbonyl groups and benzyl ester groups are removed, for example, by hydrogenation. Protective groups of the tert-butyl type are removed by acidic hydrolysis.

The conditions for forming the peptide bond are also known from peptide chemistry (cf., for example Houben-Weyl loc. cit., Ullmanns loc. cit.).

In the formation of the amide or peptide bond, a direct removal of water in the reaction of the amino component with the —COOH-containing component is possible by means of addition of suitable condensing agents, the reaction being carried out in anhydrous medium. Expediently, however, activation of the carboxyl group is carried out before or during the reaction. The activation of the carboxyl group can be carried out, for example, by the azide method or the mixed anhydride method. In the mixed anhydride method, for example, half esters of carbonic acid are used. The activation of the carboxyl group by the carbodiimide method, for example using dicyclohexylcarbodiimide (DCC), is particularly convenient, it being possible to carry out the reaction in a one-pot process. Expediently, the carbodiimide method is combined with the active ester method, i.e. an N-hydroxy compound forming an active ester, such as, for example, N-hydroxysuccinimide (HONSu), 1-hydroxybenzotriazole (HOBt) or 3-hydroxy-4-oxo-3,4-dihydro-1,2,3-benzotriazine (HOObt), is employed additionally to a carbodiimide. The use of HOBt or HOObt in combination with a carbodiimide, in particular DCC, is preferred.

The reactions are expediently carried out in a suitable inert solvent or dispersant, such as, for example, water, methanol, ethanol, acetonitrile, an amide, such as dimethylformamide or dimethylacetamide, N-methylpyrrolidone, methylene chloride or an ether, such as tetrahydrofuran, or a mixture of various solvents or dispersants.

The reactions can in principle be carried out at temperatures between −10° C. and the boiling point of the solvent or dispersant used. In many cases, the reaction is carried out at 0° to 50° C., in particular at 0° to 30° C. and preferably at 0° to room temperature.

In the preparation of the compounds of the formula I, the starting components and the activating agent or activating agent mixture optionally used are normally employed in approximately equimolar amounts.

The compounds of the formula I according to the invention form acid addition salts with inorganic or organic acids. Acids suitable for the formation of acid addition salts of this type are, for example: hydrogen chloride, hydrogen bromide, naphthalenedisulphonic acids, in particular naphthalene-1,5-disulphonic acid, phosphoric, nitric, sulphuric, oxalic, lactic, glycolic, sorbic, tartaric, acetic, salicylic, benzoic, formic, propionic, pivalic, diethylacetic, malonic, succinic, pimelic, fumaric, maleic, malic, sulphamic, phenylpropionic, gluconic, ascorbic, nicotinic, isonicotinic, methanesulphonic, p-toluenesulphonic, citric or adipic acid. The acid addition salts are prepared as usual by combination of the components, expediently in a suitable solvent, or diluent.

Carboxyl groups in the compounds of the formula I can form salts by combining in a known manner with hydroxides, such as, for example, sodium hydroxide, potassium hydroxide, rubidium hydroxide, lithium hydroxide, magnesium hydroxide, calcium hydroxide or organic amines.

The starting compounds of the formulae II and IIa can be prepared from the corresponding amino compounds by guanylation or nitroguanylation. The amino compounds are known or can be prepared from the corresponding known starting compounds by customary methods. The following reagents can be reused for guanylation and nitroguanylation:

1. O-methylisothiourea (S. Weiss and H. Krommer, Chemiker Zeitung 98 (1974) 617–618);
2. S-methylisothiourea (R. F. Borne, M. L. Forrester and I. W. Waters, J. Med. Chem. 20 (1977) 771–776);
3. nitro-S-methylisothiourea (L. S. Hafner and R. F. Evans, J. Org. Chem. 24 (1959) 1157);
4. formamidinesulphonic acid (K.Kim, Y.-T. Lin and H. S. Mosher, Tetrahedron Lett. 29 (1988) 3183–3186);
5. 3,5-dimethyl-1-pyrazolylformamidinium nitrate (F. L. Scott, D. G. O'Donovan and J. Reilly, J.Amer. Chem. Soc. 75 (1953) 4053–4054).

The starting compounds of the formulae III and IIIa are synthesised stepwise from known compounds in a known manner, as a rule from the C-terminal end. The peptide couplings can be carried out using the known coupling methods of peptide chemistry.

The compounds of the formula III can be prepared in a manner known per se, for example, by reaction of a compound of the general formula IIIb

with a compound HR.

The compounds of the formula IIIa can be prepared in a known manner, for example, by reaction of a compound of the general formula IIIc

where Y denotes hydrogen or a suitable protective group, with a sarcosine (HN(CH$_3$)CH$_2$COOH) protected in a suitable manner.

Starting compounds of the formula Ia are synthesised analogously to the compounds according to the invention. The starting compounds of the formula IV are known or can be prepared by known methods.

The novel aspartic acid derivatives of the formula I according to the,invention and their physiologically tolerable salts have the ability to inhibit the binding of fibrinogen, fibronectin and of von Willebrand factor to integrin receptors.

Integrins are cell membrane glycoproteins and mediate cell adhesion by interaction with a large number of extracelluar proteins, such as fibronectin, laminin, fibrinogen, collagen, vitronectin, and von Willebrand factor or with other cell membrane proteins, such as, for example, ICAM-1. An important receptor of the integrin family is glycoprotein IIb/IIIa localised on blood platelets (fibrinogen receptor)—a key protein in platelet-platelet interaction and thrombus formation. A central fragment in the receptor recognition sequence of these proteins is the tripeptide Arg—Gly—Asp (E. Ruoslahti and M. D. Pierschbacher, Science 238 (1987) 491–497; D. R. Phillips, I. F. Charo, L. V. Parise and L. A. Fitzgerald, Blood 71 (1988) 831–843).

The compounds of the general formula I according to the invention and their physiologically tolerable salts inhibit platelet aggregation, metastasis of carcinoma cells and osteoclast formation on bone surfaces.

The compounds of the formula I and their physiologically acceptable salts can therefore be administered to humans as medicines per se on their own, in mixtures with one another or in the form of pharmaceutical preparations which permit enteral or parenteral use and which contain, as active constituent, an effective dose of at least one compound of the formula I or of a salt thereof, in addition to one or more customary pharmaceutically innocuous excipients, fillers or diluents and optionally one or more additives.

The medicines can be administered orally, for example in the form of tablets, film tablets, coated tablets, hard and soft gelatine capsules, microcapsules, granules, powders, pellets, solutions, syrups, emulsions, suspensions, aerosols, foams, pills or pastilles. Administration can also be carried out, however, rectally, for example in the form of suppositories, or parenterally, for example in the form of injection solutions, or percutaneously, for example in the form of ointments, creams, gels, pastes, aerosols, foams, powders, tinctures, liniments or so-called transdermal therapeutic systems (TTS) or nasally, for example in the form of nasal sprays.

The pharmaceutical preparations can be prepared in a manner known per se using pharmaceutically inert inorganic or organic auxiliaries, excipients, fillers or diluents. For the preparation of pills, tablets, film tablets, coated tablets and the pellet or granule fillings of hard gelatin capsules, calcium phosphates, lactose, sorbitol, mannitol, starches, prepared starches, chemically modified starches, starch hydrolysates, cellulose, cellulose derivatives, synthetic polymers, talc etc., for example, can be used. The excipients or diluents for soft gelatine capsules and suppositories are, for example, fats, waxes, semi-solid and liquid polyols, natural or hardened oils, etc. Suitable excipients or diluents for the preparation of solutions and syrups are, for example, water, polyols, solutions of sucrose, dextrose, glucose, etc. Suitable excipients for the preparation of injection solutions are, for example, water, alcohols, glycerol, polyols or vegetable oils. Suitable excipients or diluents for ointments, creams and pastes are, for example, natural petroleum jelly, synthetic petroleum jelly, viscous and mobile paraffins, fats, natural or hardened vegetable and animal oils, neutral oils, waxes, wax alcohols, polyethylene glycols, polyacrylic acid, silicone gels, etc. Suitable excipients for microcapsules or implants are, for example, copolymers of glycolic acid and lactic acid.

Apart from the active compounds and diluents or excipients, the pharmaceutical preparations can additionally contain, in a manner known per se, one or more additives or auxiliaries, such as, for example, disintegrants, binders, lubricants, wetting agents, stabilisers, emulsifiers, preservatives, sweeteners, colorants, flavourings or aromarisers, buffer substances, and also solvents or solubilisers, solution accelerators, antifoams, salt-forming agents, gel-forming agents, thickeners, flow regulators, absorbents, agents for achieving a depot effect or agents, in particular salts, for changing the osmotic pressure, coating agents or antioxidants, etc. They can also contain two or more compounds of the formula I or their pharmalogically acceptable acid addition salts and additionally one or more other therapeutically active substances.

Other therapeutically active substances of this type are, for example, agents promoting the circulation, such as dihydroergocristine, nicergoline, buphenine, nicotinic acid and its esters, pyridylcarbinol, bencyclan, cinnarizine, naftidrofuryl, raubasine and vincamine; positively inotropic compounds, such as digoxin, acetyldigoxin, metildigoxin and lanthanoglycosides; coronary dilators, such as carbochromen; dipyramidol, nifedipine and perhexiline; antianginal compounds, such as isosorbide dinitrates, isosorbide mononitrates, glycerol nitrates, molsidomine and verapamil; $\beta$-blockers, such as propranolol, oxprenolol, atenolol, metaprolol and penbutolol. The compounds may moreover be combined with other nootropic substances, such as, for example, piracetam, or CNS-active substances, such as pirlindol, sulpiride, etc.

The content of the active compound or the active compounds of the formula I in the pharmaceutical preparations can vary within wide limits and is, for example, 0.05 to 15% by weight, preferably 0.05 to 20% by weight. In solid presentation forms, such as coated tablets, tablets, etc., the content of one or more active compounds of the formula I is in many cases 2 to 20% by weight. Liquid presentation forms, such as drops, emulsions and injection solutions often contain 0.05 to 2% by weight, preferably 0.05 to 1% by weight, of one or more active compounds of the formula I. The content of one or more active compounds of the formula I in the pharmaceutical preparations can optionally be partially replaced, for example up to 50% by weight, preferably to 5 to 40% by weight, by one or more other therapeutically active substances.

The compounds of the formula I, their physiologically acceptable salts and the pharmaceutical preparations which contain the compounds of the formula I or their physiologically acceptable salts as active compounds, can be employed in humans for the prophylaxis and therapy of, for example, arterial vascular diseases, such as acute myocardial infarct in combination with lysis therapy, post-infarct treatment, secondary prevention of myocardial infarct, reocclusion prophylaxis after lysis and dilatation, unstable angina pectoris, transitory ischaemic attacks, strokes, coronary bypass operation and reocclusion prophylaxis of bypass, pulmonary embolism, peripheral arterial occlusive diseases, dissecting aneurysm, for the therapy of venous and microcirculatory vascular disorders, such as deep vein thrombosis, disseminated intravascular clotting, post-operative and post-partum trauma, surgical or infectious shock, septicaemia, for therapy in hyperreactive platelet diseases, thrombotic thrombocytopenic purpura, preeclampsia; premenstrual syndrome, dialysis, extracorporeal circulation, and also in inflammations and in the treatment of tumours and the inhibition of osteoclast formation on the bone surface.

The dose can vary within wide limits and is to be adapted to the individual conditions in each individual case. In general, in the case of oral administration a daily dose of about 0.1 to 1 mg/kg, preferably 0.3 to 0.5 mg/kg, of body weight is appropriate to achieve effective results, in the case of intravenous administration the daily dose is in general about 0.01 to 0.3 mg/kg, preferably 0.05 to 0.1 mg/kg, of body weight. The daily dose is normally divided, in particular in the case of the administration of relatively large amounts, into several, for example 2, 3 or 4, part administrations.

In some cases, depending on individual behaviour, it may be necessary to deviate upwards or downwards from the given daily dose. Pharmaceutical preparations normally contain 0.2 to 50 mg, preferably 0.5 to 10 mg, of active compound of the general formula I or one of its pharmaceutically acceptable acid addition salts per dose.

The compounds of the formula I are in particular tested for their inhibiting action in blood platelet aggregation and the adhesion of fibrinogen to blood platelets. The measurement of aggregation and the binding of $^{125}$I-fibrinogen is carried out on filtered, plasma-free human platelets. Platelet activation is effected by means of ADP or thrombin.

As a functional test, the inhibition of aggregation of filtered human platelets is measured after ADP or thrombin stimulation by the compounds according to the invention. The IC$_{50}$ value of inhibition is given.

Reference: G. A. Marguerie et al., J. Biol. Chem. 254 (1979), 5357–5363

The K$_i$ value of the inhibition of binding of $^{125}$I-fibrinogen after stimulation with ADP (10 μm) is given.

Reference: J. S. Bennett and G. Vilaire, J. Clin. Invest. 64, (1979), 1393–1401.
E. Kornecki et al., J. Biol. Chem. 256 (1981), 5695–5701
G. A. Marguerie et al., J. Biol. Chem. 254 (1979), 5357–5363
G. A. Marguerie et al., J. Biol. Chem. 255 (1980), 154–161

In the testing of the inhibition of fibrinogen formation and the inhibition of aggregation, the following results are obtained for the compounds of the following examples:

| Example | Inhibition of platelet aggregation | | Inhibition of fibrinogen binding |
|---|---|---|---|
| | ADP (μM) | Thrombin (μM) | K$_i$ (μM) |
| 1 | 8 | 2 | * |
| 2 | 15 | 10 | * |
| 3 | 15 | 5 | * |
| 4 | 20 | 15 | 10 |
| 9 | 2 | 2 | 1.8 |
| 12 | 8 | 4 | 3.1 |
| 14 | 4.5 | 1.5 | 0.8 |

*: not measured

In the examples below, the following abbreviations, inter alia, are used:
Asp=aspattic acid
Val=valine
Bn=benzyl
HOBt=1-hydroxybenzotriazole
DMF=dimethylformamide
DCC=dicyclohexylcarbodiimide
DCH=dicyclohexylurea
Sarc=sarcosine

EXAMPLES

Example 1 p-(4-(N-Amidinopiperidinyl)methyl)benzoyl-L-aspartyl-L-valine a) p-(4-(Nitroamidinopiperidinyl)methyl)benzoic acid 3.42 g (25.3 mmol) of nitro-S-methylisothiourea are added at 0° C. with stirring to a solution of 4.96 g (22.6 mmol) of p-(4-piperidinylmethyl)benzoic acid and 1.81 g (45.2 mmol) of NaOH in 50 ml of water. After stirring at room temperature for 24 h, the mixture is acidified to pH=1 with conc. HCl. The precipitate is filtered off, washed with water and dried.

Yield: 6.13 g (89%); melting point: 260° to 261° C. (dec).

b) p-(4-N-Nitroamidinopiperidinyl)methyl)benzoyl-AsP(OBn)-Val—OBn 0.83 g (3.64 mmol) of DCC are added at 0° C. to a solution of 1.11 g (3.64 mmol) of p-(4-(nitroamidinopiperidinyl)methyl)benzoic acid, 1.50 g (3.64 mmol) of H$_2$N-Asp(OBn)-Val-OBn and 0.49 g (3.64 mmol) of HOBt in 25 ml of DMF. After stirring at 0° C. for 4 h, the mixture is stirred at room temperature for a further 12 h. The precipitated DCH is filtered off and the residue is purified by chromatography.

Yield: 2.43 g (95%), still contains some DCH; melting point: 60° to 75° C.

c) p-(4-N-Amidinopiperidinyl)methyl)benzoyl-L-aspartyl-L-valine 2.29 g (3.27 mmol) of p-(4-(N-nitroamidinopiperidinyl)methyl)-benzoyl-Asp(OBn)-Val-OBn are dissolved in 20 ml of methanol/10 ml of DMF and treated with 0.25 g of Pd/C (10%): After hydrogenation at room temperature for 6 h, 20 ml of water and 20 ml of glacial acetic acid are added and the mixture is hydrogenated for a further 1.5 h. The catalyst is filtered off and the residue is chromatographed on ®Sephadex LH-20 (methanol).

Yield: 1.47 g (94%); melting point: 260° to 270° C.; $[\alpha]_D^{20} = -5.5°$ (c=1 in glacial acetic acid)

Example 2 p-(4-(N-Amidinopiperidinyl)methyl)benzoyl-L-aspartylcyclohexylamide a) p-(4-(N-Nitroamidinopiperidinyl)methyl)benzoyl-Asp(OBn)-cyclohexylamide Analogously to 1b), 1.51 g (4.93 mmol) of p-(4-(nitroamidinopiperidinyl)methyl)benzoic acid are allowed to react with 1.50 g (4.93 mmol) of H$_2$N-Asp(OBn)cyclohexylamide.

Yield: 2.3 g (79%); melting point: 70° to 75° C.

b) p-(4-N-Amidinopiperidinyl)methyl)benzoyl-L-aspartyl-cyclohexylamide 2.1 g (3.54 mmol) of p-(4-N-nitroamidinopiperidinyl)-methyl)benzoyl-Asp(OBn)cyclohexylamide are hydrogenated analogously to 1c).

Yield: 1.6 g (82%); melting point: 220° to 225° C.; $[\alpha]_D^{20} = -5.8°$ (c=1.2 in glacial acetic acid)

Example 3 p-(4-N-Amidinopiperidinyl)methyl)benzoyl-L-aspartyl-3,3-diphenylpropylamide a) p-(4-N-Nitroamidinopiperidinyl)methyl)benzoyl-Asp(OBn)-3,3-diphenylpropylamide Analogously to 1b), 1.1 g (3.6 mmol) of p-(4-(nitroamidinopiperidinyl)methyl)benzoic acid are allowed to react with 1.50 g (3.6 mmol) of H$_2$N-Asp(OBn)-3,3-diphenylpropylamide.

Yield: 2.15 g (85%) of acetate; melting point: 90° to 100° C.

b) D-(4-N-Amidinopiperidinyl)methyl)benzoyl-L-aspartyl-3,3-diphenylpropylamide 1.97 g (2.8 mmol) of p-(4-(N-nitroamidinopiperidinyl)methyl)-benzoyl-Asp(OBn)-3,3-diphenylpropylamide are hydrogenated analogously to 1c).

Yield: 1.57 g (89%) of acetate; melting point: 160° to 175° C.; $[\alpha]_D^{20} = -6.4°$ (c=1.1 in glacial acetic acid)

The following were prepared analogously:

Example 4 p-(4-N-Amidinopiperidinyl)methyl)benzoyl-L-aspartyl-isopropylamide

Melting point: 206° to 208° C.; $[\alpha]_D^{20} = +5.6°$ (c=1.2 in glacial acetic acid)

Example 5 p-(2-Guanidinoethyl)phenoxyacetyl-L-aspartyl-cyclohexylamide a) p-(2-Nitroguanidinoethyl)phenoxyacetyl-L-AsP(OBn)-cyclohexyl amide Analogously to 1b), 1.48 g (5.26 mmol) of p-(2-nitroguanidinoethyl)phenoxy acetic acid are allowed to react with 1.60 g (5.26 mmol) of H$_2$N-Asp(OBn)cyclohexylamide.

Yield: 2.51 g (84%); melting point: 140° to 144° C.

b) p-(2-Guanidinoethyl)phenoxyacetyl-L-aspartyl-cyclohexylamide 1.4 g (2.46 mmol) of p-(2-nitroguanidinoethyl)-phenoxyacetyl-L-Asp(OBn)cyclohexylamide are hydrogenated analogously to 1c).

Yield: 0.6 g (56%); melting point: 215° to 219° C.; $[\alpha]_D^{20} = +4°$ (c=1 in glacial acetic acid)

The following were prepared analogously to Example 5:

Example 6 p-(2-Guanidinoethyl)phenoxyacetyl-L-aspartyl-3,3-diphenylpropylamide melting point: 194° C. (dec.); $[\alpha]_D^{20} = +3.5°$ (c=1.1 in glacial acetic acid)

Example 7 p-(2-Guanidinoethyl)phenoxyacetyl-L-aspartyl-D,L-β-phenyl-β-alanine ethyl ester $[\alpha]_D^{20} = +9.1°$ (c=1 in glacial acetic acid)

Example 8 p-(2-Guanidinoethyl)phenoxyacetyl-L-aspartyl-amido-cyclohexan-1-carboxylic acid

Melting point: 190° to 199° C.; $[\alpha]_D^{20} = -4.8°$ (c=1.2 in glacial acetic acid)

Example 9 p-Guanidinomethylbenzoylsarcosyl-L-aspartyl-3,3-diphenylpropylamide a) p-Nitroquanidinoethylbenzoyl-Sarc-Asp(OBn)-3,3-diphenylpropylamide Analogously to 1b), 0.59 g (2.48 mmol) of p-nitroguanidinomethylbenzoic acid is allowed to react with 1.21 g (2.48 mmol) of H$_2$N-Sarc-Asp-(OBn)-3,3-diphenylpropylamide.

Yield: 1.37 g (78%).

b) D-Guanidinomethylbenzoylsarcosyl-L-aspartyl-3,3-diphenylpropylamide 1.25 g (1.77 mmol) of p-nitroguanidinoethylbenzoyl-Sarc-Asp-(OBn)-3,3-diphenylpropylamide are hydrogenated analogously to 1c).

Yield: 0.60 g (54%); melting point: 180° to 195° C.; $[\alpha]_D^{20} = -17.6°$ (c=1 in glacial acetic acid)

Example 10 p-Guanidinomethylbenzoylsatcosyl-L-aspartyl-amido-cyclohexane-1-carboxylic acid

Melting point: 180° to 185° C.; $[\alpha]_D^{20} = -25.8°$ (c=1 in glacial acetic acid)

Example 11 trans-4-Guanidinomethylcyclohexanecarboxylsarcosyl-L-aspartyl-amido-cyclohexane-1-carboxylic acid a) Benzyl trans-4-nitroguanidinomethylcyclohexanecarboxyl-Sarc-Asp(OBn)-amidocyciohexane-1-carboxylate Analogously to 1b), 0.48 g (1.96 mmol) of trans-4-nitroguanidinomethylcyclohexane-1-carboxylic acid is allowed to react with 1.00 g (1.96 mmol) of benzyl H$_2$N-Sarc-Asp(OBn)amidocyclohexane-1-carboxylate.

Yield: 1.25 g (87%).

b) trans-4-Guanidinomethylcyclohexanecarboxylsarcosyl-L-aspartyl-amidocyclohexane-1-carboxylic acid 1.13 g (1.54 mmol) of benzyl trans-4-Nitroguanidinomethylcyclo-hexanecarboxyl-Sarc-Asp(OBn)-amidocyclohexane-1-carboxylate are hydrogenated analogously to 1c).

Yield: 0.83 g (94%); melting point: 210° to 220° C.; $[\alpha]_D^{20} = -24.6°$ (c=11 in glacial acetic acid)

Example 12 trans-4-Guanidinomethylcyclohexanecarboxylsarcosyl-L-aspartylbenzhydrylamide $[\alpha]_D^{20} = -22.8°$ (c=1.1 in glacial acetic acid)

Example 13 p-(2-Guanidinoethyl)phenoxyacetyl-L-aspartyl-D,L-β-phenyl-βalanine a) p-(2-Nitroguanidinoethyl)phenoxyacetyl-L-Asp(OBn)-D,L-β-phenyl-β-alanine benzyl ester Analogously to 1b), 0.92 g (3.26 mmol) of p-(2-nitroguanidinoethyl)phenoxy acetic acid is allowed to react with 1.5 g (3.26 mmol) of H$_2$N-Asp(OBn)-D,L-β-phenyl-β-alanine benzyl ester.

Yield: 1.28 g (54%).

b) p-(2-Guanidinoethyl)phenoxyacetyl-L-aspartyl-D,L-β-phenyl-β-alanine 1.24 g (1.71 mmol) of p-(2-nitroguanidinoethyl)-phenoxyacetyl-L-Asp(OBn)-D,L-β-phenyl-β-alanine benzyl ester are hydrogenated analogously to 1c).

Yield: 0.58 g (68%); melting point: 155° to 175° C.; $[\alpha]_D^{20}$ 0.03° (c=1 in glacial acetic acid)

Example 14 p-(4-N-Amidinopiperidinyloxy)benzoyl-L-aspartyl-L-valine a) p(4-N-Nitroamidinopiperidinyloly)benzoyl-L-Asp(OBn)-L-Val-OBn Analogously to 1b), 0.3 g (=0.97 mmol) of p-(4-N-nitroamidinopiperidinyloxy)benzoic acid is allowed to react with 0.4 g (0.97 mmol) of H$_2$N-Asp(OBn)-Val-OBn.

Yield: 0.55 g (81%).

b) p-(4-N-Amidinopiperidinyloxybenzoyl-L-aspartyl-L-valine 0.36 g (0.51 mmol) of p-(4-N-nitroamidinopiperidinyloxy)benzoyl-L-Asp(OBn)-L-Val-OBn is hydrogenated analogously to 1c).

Yield: 0.23 g (94%); melting point: 150° C.

Example 15 p-4-N-Amidinopiperidinylbenzoyl-L-aspartyl-L-valine a) p-4-Nitroamidinopiperidinylbenzoyl-Asp(OBn)-L-Val-OBn Analogously to 1b), 2.5 g (8.55 mmol) of p-4-nitroamidinopiperidinylbenzoic acid are allowed to react with 3.56 g (8.55 mmol) of H$_2$N-Asp(OBn)-Val-OBn.

Yield: 1.92 g (25%).

b) p-4-N-Amidinopiperidinylbenzoyl-L-aspartyl-L-valine

Analogously to 1c), 0.42 g (0.61 mmol) of p-4-nitroamidinopiperidinylbenzoyl-Asp(OBn)-L-Val-OBn is hydrogenated.

Yield: 0.14 g (41%); melting point: 190° C. (dec.).

Example 16 p-(3-N-Amidinopyrvolidinyloxy)benzoyl-L-aspartyl-L-valine a) p-(3-N-Nitroamidinopyrvolidinyloxy)benzoyl-L-Asp(OBn)-L-Val-OBn Analogously to 1b), 0.29 g (0.99 mmol) of p-(3-N-nitroamidinopyrvolidinyloxy)benzoic acid is allowed to react with 0.41 g (0.99 mmol) of H$_2$N-Asp(OBn)-Val-OBn.

Yield: 0.63 g (92%).

b) p-(3-N-Amidinopyrvolidinyloxy)benzoyl-L-aspartyl-L-valine 0.63 g (0.92 mmol) of p-(3-N-nitroamidinopyrvolidinyloxy)benzoyl-L-Asp(OBn)-L-Val-OBn is hydrogenated analogously to 1c).

Yield: 0.11 g (27%); melting point: 250° C.; $[\alpha]_D^{20} = -5.95°$ (C=0.84 in methanol/water 2:1).

The following examples A to H relate to pharmaceutical preparations.

Example A

Emulsions containing 3 mg of active compound per 5 ml can be prepared according to the following recipe:

| | |
|---|---|
| Active compound | 0.06 g |
| Neutral oil | q.s. |
| Sodium carboxymethylcellulose | 0.6 g |
| Polyoxyethylene stearate | q.s. |
| Pure glycerol | 0.6 to 2 g |
| Flavourings | q.s. |
| Water (demineralized or distilled) | to 100 ml |

Example B

Tablets can be prepared according to the following formulation:

| | |
|---|---|
| Active compound | 2 mg |
| Lactose | 60 mg |
| Maize starch | 30 mg |
| Soluble starch | 4 mg |
| Magnesium stearate | 4 mg |
| | 100 mg |

Example C

The following composition is suitable for the production of soft gelatine capsules containing 5 mg of active compound per capsule:

| | |
|---|---|
| Active compound | 5 mg |
| Mixture of triglycerides of coconut oil | 150 mg |
| Capsule contents | 155 mg |

Example D

The following formulation is suitable for the production of coated tablets:

| | |
|---|---|
| Active compound | 3 mg |
| Maize starch | 100 mg |
| Lactose | 55 mg |
| sec. Calcium phosphate | 30 mg |
| Soluble starch | 3 mg |
| Magnesium stearate | 5 mg |
| Colloidal silica | 4 mg |
| | 200 mg |

Example E

Coated tablets, containing a compound according to the invention and another therapeutically active substance:

| | |
|---|---|
| Active compound | 6 mg |
| Propanolol | 40 mg |
| Lactose | 90 mg |
| Maize starch | 90 mg |
| sec. Calcium phosphate | 34 mg |
| Soluble starch | 3 mg |
| Magnesium stearate | 3 mg |
| Colloidal silica | 4 mg |
| | 270 mg |

Example F

Coated tablets, containing a compound according to the invention and another therapeutically active substance:

| | |
|---|---|
| Active compound | 5 mg |
| Pirlindol | 5 mg |
| Lactose | 60 mg |
| Maize starch | 90 mg |
| sec. Calcium phosphate | 30 mg |
| Soluble starch | 3 mg |
| Magnesium stearate | 3 mg |
| Colloidal silica | 4 mg |
| | 200 mg |

Example G

Capsules, containing an active compound according to the invention and another therapeutically active substance:

| | |
|---|---|
| Active compound | 5 mg |
| Nicergoline | 5 mg |
| Maize starch | 185 mg |
| | 195 mg |

Example H

Injection solutions containing 1 mg of active compound per ml can be prepared according to the following recipe:

| Active compound | 1.0 mg |
|---|---|
| Polyethylene glycol 400 | 0.3 mg |
| Sodium chloride | 2.7 mg |
| Water for injection purposes to | 1 ml |

It is to be understood that the above described embodiments of the invention are illustrative only, and that modifications thereof may occur to those skilled in the art. Accordingly, this invention is not to be regarded as limited to the embodiments disclosed herein, but is to be limited only as defined by the appended claims.

We claim:

1. Aspartic acid derivatives of the general formula I

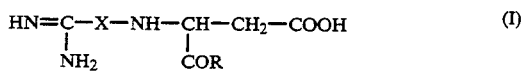 (I)

in which
X denotes

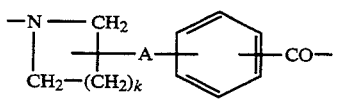

A denotes $-(CH_2)_m-$, $-O-$ or a direct bond,
k=2 or 3,
m denotes a number from 0 to 4,
R denotes

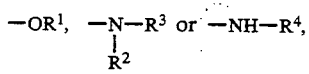

$R^1$ denotes hydrogen, $C_1-C_6$ alkyl, $C_3-C_8$ cycloalkyl, phenyl, where the $C_1-C_6$ alkyl, the $C_3-C_8$ cycloalkyl or the phenyl is unsubstituted or mono- or di-substituted by identical or different radicals selected from the group consisting or hydroxyl, carboxyl, $C_1-C_4$ alkoxycarbonyl, phenylmethoxycarbonyl, carboxamido, $C_1-C_4$ alkylaminocarbonyl, amine, mercapto, $C_1-C_4$ alkoxy, $C_3-C_8$ cycloalkyl, imidazolyl, indolyl, pyrrolidinyl, hydroxypyrrolidinyl, halogen, phenyl or phenoxy, each of which is unsubstituted or monosubstituted or di-substituted by hydroxyl, $C_1-C_4$ alkyl, halogen, nitro or trifluoromethyl;

$R^2$ and $R^3$ independently of one another denote hydrogen or $R^1$; and $R^4$ denotes the radical of an amine acid selected from the group consisting of Aad, Abu, βAbu, ABz, 2ABz, εAca, Ach, Acp, Adpd, Ahb, Aib, βAib, Ala, βAla, ΔAla, Alg, All, Ama, Amt, Ape, Apm, Apr, Arg, Asn, Asp, Asa, Aze, Azi, Bai, Bph, Can, Cit, Cys, (Cys)$_2$, Cyta, Daad, Dab, Dadd, Dap, Dapm, Dasu, Dien, Dpa, Dtc, Fel, Gln, Glu, Gly, Guy, hAla, hArg, hCys, hGln, hGlu, Ilis, hIle, hLeu, hLys, hMet, hPhe, hPro, hScr, hThr, hTrp, hTyr, Hyl, Hyp, 3Hyp, Ile, Ise, Iva, KVn, Lant, Lcn, Leu, Lsg, Lys, βLys, ΔLys, Met, Mim, Min, nArg, Nle, Nva, Oly, Orn, Pan, Pec, Pen, Phe, Phg, Pic, Pro, ΔPro, Pse, Pys, Pyr, Pza, Oin, Ros, Sar, Sec, Sem, Ser, Thi, βThi, Thr, Thy, Thx, Tia, Tle, Tly, Trp, Trta, Tyr, Val, Tbg, Npg, Chg, Cha, Thia, 2,2-diphenylaminoacetic acid, 2- (tolyl)-2-phenylaminoacetic acid, 2-(p-chlorophenyl) aminoacetic acid, or of a dipeptide thereof, in which the peptide bond can also be reduced to $-NH-CH_2-$; and their physiologically tolerable salts.

2. Compounds according to claim 1, characterised in that the radicals representing X contain p-piperidinyl or 3-pyrrolidinyl.

3. Compounds according to claim 1, characterised in that k=3 and m=1 or 2.

4. Compounds according to claim 1, characterised in that R denotes $-N(R^2)R^3$ or $-NHR^4$.

5. Compounds according to claim 1, characterised in that R denotes $-NHR^4$, where $R^4$ represents the valine, phenylalanine or phenylglycine radical, which is formally formed by removal of the amino group from valine, phenylalanine or phenylglycine.

6. Compounds according to claim 1 in which the phenylene group of the X radical is a 1,4- or 1,3-phenylene group.

7. Compounds according to claim 1 in which k=2 and m=1 or 2.

8. p (4-N-Amidinopiperidinyloxy)benzoyl-L-aspartyl-L-valine.

9. Process for inhibiting platelet aggregation, comprising administering to a patient in need thereof an effective dose of a compound according to claim 1.

10. Pharmaceutical preparation, characterised in that it contains one or more compounds of the general formula I of claim 1 or a physiologically tolerable salt thereof as active compound together with pharmaceutically acceptable excipients and additives.

* * * * *